United States Patent
Willert et al.

(10) Patent No.: US 8,535,358 B2
(45) Date of Patent: Sep. 17, 2013

(54) BONE SCREW AND METHOD FOR MANUFACTURING THE SAME

(75) Inventors: Wayne A. Willert, Port Washington, NY (US); Andrea Willert, Port Washington, NY (US)

(73) Assignee: Medical Facets, LLC, Port Washington, NY (US)

( * ) Notice: Subject to any disclaimer, the term of this patent is extended or adjusted under 35 U.S.C. 154(b) by 0 days.

(21) Appl. No.: 13/369,760

(22) Filed: Feb. 9, 2012

(65) Prior Publication Data

US 2012/0172935 A1 Jul. 5, 2012

Related U.S. Application Data

(63) Continuation-in-part of application No. 11/985,960, filed on Nov. 19, 2007, now Pat. No. 8,112,870.

(51) Int. Cl.
*A61B 17/86* (2006.01)
*B23G 1/02* (2006.01)

(52) U.S. Cl.
USPC ........................................................ 606/309

(58) Field of Classification Search
USPC ................. 411/411, 413, 308–311, 417, 420, 411/421; 433/172–174, 73, 201.1; 606/300–331
See application file for complete search history.

(56) References Cited

U.S. PATENT DOCUMENTS

| | | | |
|---|---|---|---|
| 2,393,131 A | 1/1946 | Vang | |
| 3,201,967 A | 8/1965 | Balamuth et al. | |
| 3,783,668 A | 1/1974 | Dawson et al. | |
| 3,879,974 A | 4/1975 | Biddell et al. | |
| 4,103,422 A * | 8/1978 | Weiss et al. | 433/215 |
| 4,419,912 A | 12/1983 | Sotome et al. | |
| 4,782,688 A | 11/1988 | Kawashima | |
| 5,159,167 A | 10/1992 | Chaikin et al. | |
| 5,288,714 A | 2/1994 | Marschke | |
| 5,725,573 A | 3/1998 | Dearnaley et al. | |
| 6,273,722 B1 * | 8/2001 | Phillips | 433/174 |
| 6,431,869 B1 | 8/2002 | Reams et al. | |
| 6,450,748 B1 | 9/2002 | Hsu | |
| 6,481,760 B1 * | 11/2002 | Noel et al. | 285/334 |
| 6,595,733 B1 | 7/2003 | Willert | |
| 6,726,689 B2 * | 4/2004 | Jackson | 606/916 |
| 7,101,134 B2 * | 9/2006 | LeVey et al. | 411/411 |
| 7,217,195 B2 | 5/2007 | Matsubayashi | |
| 7,281,925 B2 * | 10/2007 | Hall | 433/174 |
| 7,559,221 B2 | 7/2009 | Horita et al. | |
| 7,875,285 B1 | 1/2011 | Roorda et al. | |
| 7,879,086 B2 | 2/2011 | Davis | |
| 7,901,453 B2 | 3/2011 | Ragheb et al. | |
| 7,913,642 B2 | 3/2011 | O'Connor et al. | |
| 7,935,138 B1 * | 5/2011 | Richelsoph | 606/313 |
| 8,028,646 B2 | 10/2011 | Pui et al. | |
| 8,112,870 B2 * | 2/2012 | Willert et al. | 29/557 |

(Continued)

*Primary Examiner* — Kevin T Truong
*Assistant Examiner* — Christopher Beccia
(74) *Attorney, Agent, or Firm* — Tutunjian & Bitetto, P.C.

(57) ABSTRACT

A bone screw and a method for manufacturing the same includes a screw thread configuration having one or more grooves cut into a leading face of the thread, a trailing face of the thread, and/or the shaft between the threads. Other implementations include the incorporation of facets into the one or more grooves. The implementation of the one or more grooves increases the surface are of the orthopedic screw and functions to increase in anchoring the bone screw within the bone once inserted therein, and thereby reduce the possibility for the screw backing out after insertion.

4 Claims, 17 Drawing Sheets

(56) References Cited

U.S. PATENT DOCUMENTS

| | | | |
|---|---|---|---|
| 8,197,255 B2* | 6/2012 | Fromovich et al. | 433/174 |
| 8,221,119 B1* | 7/2012 | Valen | 433/174 |
| 2004/0121848 A1 | 6/2004 | Zhang | |
| 2005/0076751 A1 | 4/2005 | Panasik et al. | |
| 2005/0208095 A1 | 9/2005 | Hunter et al. | |
| 2006/0162142 A1 | 7/2006 | Manuel | |
| 2006/0225477 A1 | 10/2006 | Takemasu et al. | |
| 2008/0004693 A1 | 1/2008 | Burgess et al. | |
| 2010/0174323 A1* | 7/2010 | Fourcault et al. | 606/304 |
| 2010/0190138 A1* | 7/2010 | Giorno | 433/174 |

* cited by examiner

BONE SCREW AND METHOD FOR MANUFACTURING THE SAME

CROSS REFERENCE TO RELATED APPLICATIONS

This application is a Continuation-in-Part of U.S. patent application Ser. No. 11/985,960 filed on Nov. 19, 2007 now U.S. Pat. No. 8,112,870.

BACKGROUND

1. Technical Field

The present principles relate to orthopedic (bone) screws. More particularly, it relates to an orthopedic screw with increased surface area threading and the method for making the same.

2. Description of Related Art

Medical screws or Orthopedic (bone) screws or threaded pins are commonly used in orthopedic procedures where it is required to set a bone or multiple bones in a position that is secure with respect to either 1) the adjacent bone or bone part for which the screw is used; or 2) the surgical splint or other external fixation device that is maintained in position using the bone or orthopedic screw. As used herein, the term "bone screw" and/or "orthopedic screw" are interchangeably used herein and shall include all known medical/orthopedic screws, threaded pins and/or implants of any kind that are used in human and/or animal bones.

One common concern in the use of bone screws is the splitting of the bone during the insertion of the screw. Splitting often occurs when the workpiece (e.g., bone) is brittle by nature, and the friction between the screw and the bone requires higher torques to sufficiently penetrate the bone for proper application.

Another concern is the potential for the screws to loosen or "back out" after installation. This loosening can result in the mis-setting of a bone and require supplemental procedures to be performed to correct the same.

It is would therefore be desirable to have a bone screw that eliminates these problems without requiring any change in the current approved procedures for the installation and withdrawal of such bone screws.

SUMMARY

The faceted bone screw of the present principles will also reduce the likelihood of bone screws and threaded pins backing out of the bone due to improved osteointegration between the faceted threaded portion of the implanted device and the bone.

According to one implementation, the method of manufacturing an orthopedic screw includes loading a bar stock of material into a screw cutting machine, moving a cutting tool into contact with the bar stock for a predetermined amount of time to cut a portion of the thread, removing the cutting tool from cutting contact with the bar stock before the end of the predetermined amount of time, rotating either the bar stock or cutting tool, moving the cutting tool back into contact with the bar stock for a second predetermined amount of time to cut another portion of the thread, and removing the cutting tool from cutting contact with the bar stock before the end of the second predetermined amount of time. The cutting of the bar stock is performed such that at least two adjacent cuts have different radii with respect to a central axis of the bar stock.

Other aspects and features of the present principles will become apparent from the following detailed description considered in conjunction with the accompanying drawings. It is to be understood, however, that the drawings are designed solely for purposes of illustration and not as a definition of the limits of the present principles, for which reference should be made to the appended claims. It should be further understood that the drawings are not necessarily drawn to scale and that, unless otherwise indicated, they are merely intended to conceptually illustrate the structures and procedures described herein.

BRIEF DESCRIPTION OF THE DRAWINGS

In the drawings wherein like reference numerals denote similar components throughout the views.

DETAILED DESCRIPTION

Figure 1:
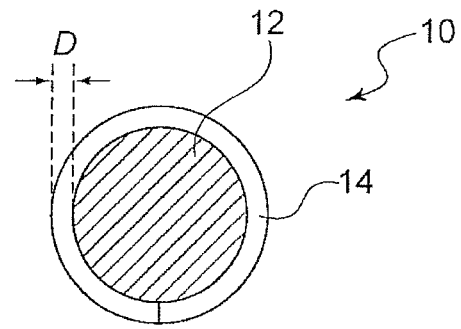
FIG. 1 is cross sectional view of a bone screw according to the prior art.

FIG. 1 shows a cross section of a bone screw 10 according to the prior art. The shaft 12 includes a thread 14 that can extend any length of the shaft 12, including the entire length of the same. The thread generally has a consistent non-variable depth D depending on the particular application for that screw. The pitch, which relates to the distance between adjacent threads, is also generally consistent for most bone screws and fasteners.

Those of ordinary skill in the art will recognize that one or more different portions of the shaft 12 can include threads 14, or alternatively the entire shaft 12 can be threaded. These same concepts apply to the bone screw of the present principles.

Figure 2A:
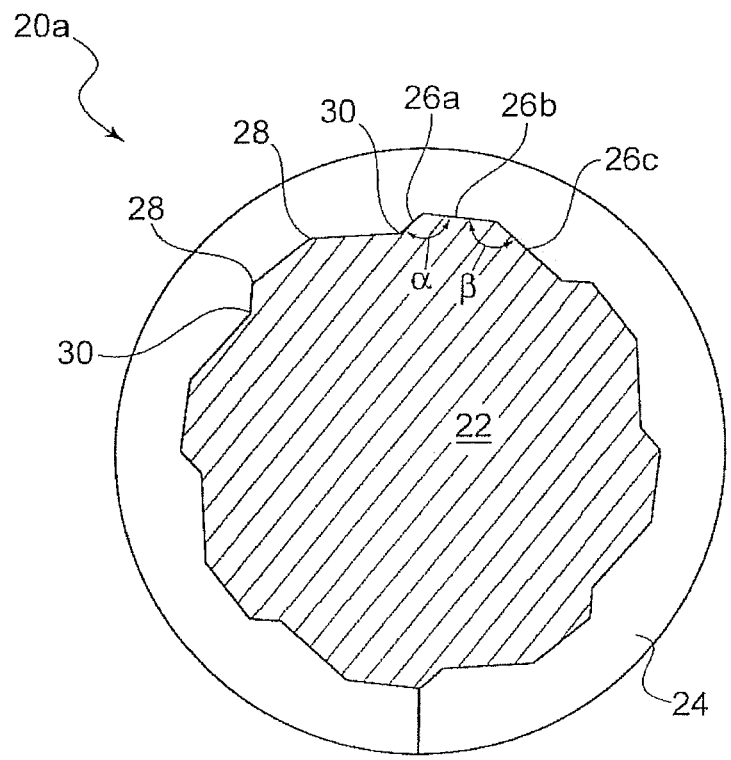
FIGS. 2a and 2b are cross-sectional views of a faceted bone screw according to an implementation of the present principles.

FIG. 2a shows a cross section of a faceted bone screw 20 according to an implementation of the present principles. The bone screw 20 has a shaft 22 having threads 24 which include one or more facets 26a, 26b and 26c. These facets are generally transverse to the thread groove and extend across the same for some or part of the overall thread length. Although shown transverse to the thread, it is contemplated that the facets may be offset from a pure transverse relationship with the thread groove. By incorporating facets 26 into the shaft within the thread groove 24, a plurality of peaks 28 and valleys 30 are formed therein. The facets 26 are disposed at different angles α and β with respect to the next adjacent facet. The angles a can be in a range of 90-170 degrees while the angles B can be in a range of 100-175 degrees. The implementation of the facets 26 will provide for a varying depth D of the thread.

As shown, there are several peaks 28 and valleys 30 formed by the facets 26 at varying depths within the thread, each having rising/falling sides depending on the direction of rotation of the shaft 22. These peaks and valleys, in conjunction with the rising/falling sides operate to reduce the friction between the bone and the screw and thereby operate to reduce the torque required to drive the bone screw into and remove from a bone. As will be appreciated, when the shaft 22 is rotated in one direction, the rising sides of the respective peaks will gradually operate to penetrate the bone and once the peak is met, the friction between the bone and the screw thread is substantially reduced as the bone passes over the falling side of that peak.

By repeating this process in a series like configuration throughout the thread, the overall torque required to drive the bone screw can be reduced by up to 50% (depending on the size of the screw and the bone being penetrated).

Once inserted into the bone, the bone will permit osteointegration with the facets 26 (including the peaks and valleys), and the facets become like anchors for preventing the screw from loosening (i.e., "backing out") after inserted by the doctor. However, when the bone screw must be extracted, a simple application of torque in the loosening direction will cause the bone to loosen or break free from the facets 26, and facets will once again operate to reduce the torque in required in the removal of the bone screw.

Figure 2B:
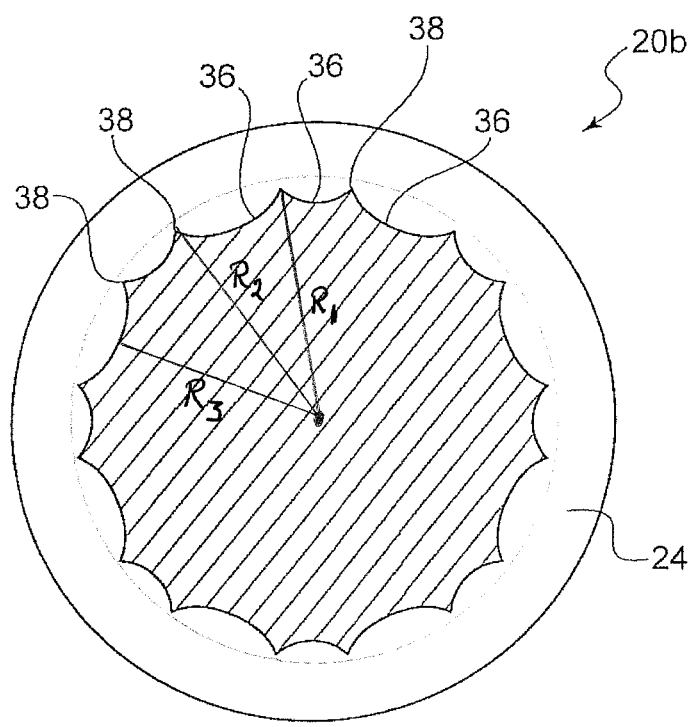

FIG. 2b shows another implementation of the bone screw 20 where the facets 36 are concave in nature and the peaks are designated by the points 38 between the respective concave facets 36. In this implementation, the valleys would be considered at the base of each concave facet 36, and the friction reduction would be omni-directional (i.e., work the same in both clockwise and counterclockwise directions). As shown, there are differing radii R1, R2, R3, etc. that results from the formation of the concave facets 36 and the corresponding peaks and valleys.

In order to manufacture the bone screw in a reproducible, certifiable manner, a precise manufacturing technique is employed using a Swiss type screw machine tool. Those of ordinary skill in the art will recognize that this time tuning (i.e., lathe) or multiple axis Swiss type CNC (Computer Numerically Controlled) screw machine is only one example of the type of machine that could be properly configured to manufacture the faceted bone screw disclosed herein, and that other types of machines may also be implemented without departing from the spirit of the present principles.

Figure 3A:
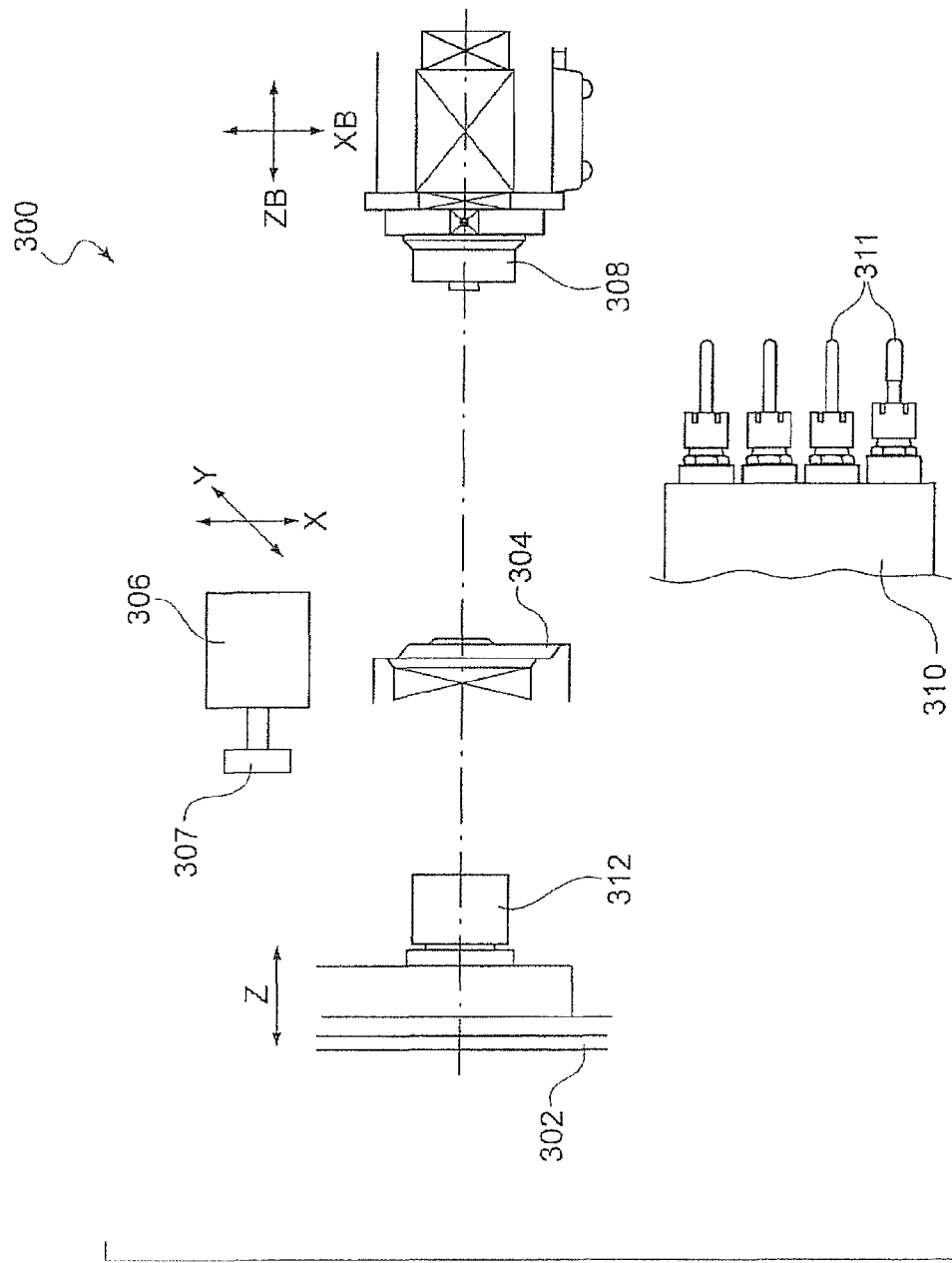
FIG. 3a is a plan view of the bone screw cutting machine that is used to manufacture the bone screw according to an implementation of the present principles.

FIG. 3a shows a plan view of a Swiss cutting machine 300 used to manufacture the bone screw of the present principles. This is the sliding headstock type CNC automatic lathe that is generally composed of a headstock 302, a guide bushing (or guide collet) 304, a live tool holder 306, a sub spindle 308, and a tool holder slide 310. The tool holder slide includes one or more tools or dies 311 that can be used during other cutting processes. Although shown here for exemplary purposes, the present principles may not require the tool holder slide 310 during the process of manufacturing the faceted bone screw.

The headstock 302 includes a main spindle 312 and a sliding unit (not shown). The main spindle 312 chucks a bar with the guide bushing 304 and provides it with rotary motion. The sliding unit provides reciprocating action on the material in the Z-axis direction (longitudinal) with the CNC control. Feeding of a bar in the ZI axis direction is provided by the headstock during the main machining. The live tool holder 306 includes a tool or cutter 307 that cuts the thread onto the (wires) bar stock used to form the same.

Figure 3B:
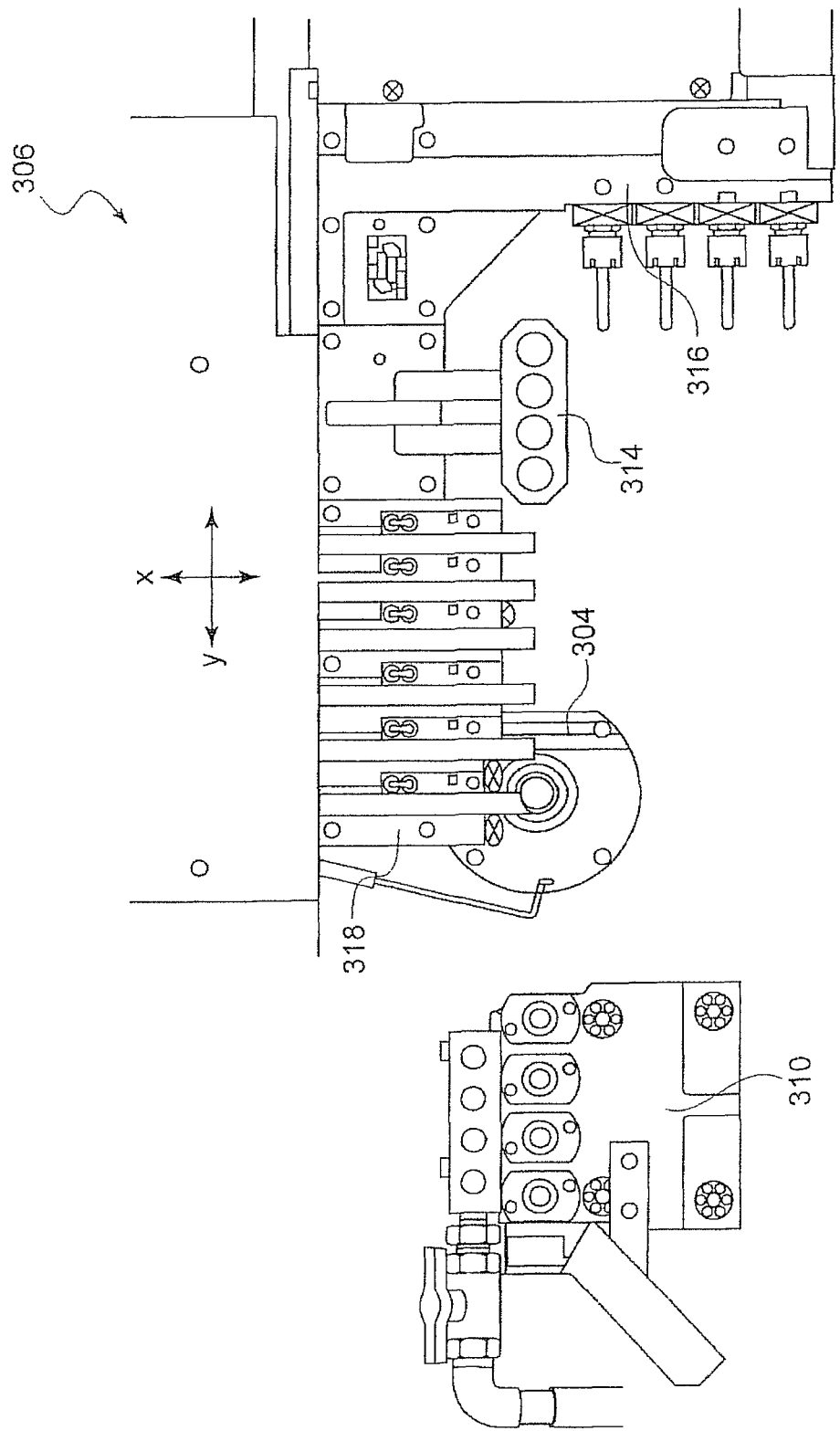
FIG. 3b is a plan view of the bone screw cutting machine that is used to manufacture the bone screw according to an implementation of the present principles.

FIG. 3b shows a plan view of the live tool holder 306 of the Screw cutting lathe/machine 300. The live tool holder is capable of reciprocating motion in the X-axis and Y-axis under the CNC Control, and will feed material in a diametric direction during main machining. The tool post makes the cutting tool contact the bar near the guide bushing 304 and cooperates with the headstock 302 to execute the machining. The tool holder (not shown), the 4-spindle sleeve holder 314 and the 4-spindle cross drilling/milling unit 316 are attached to the tool post. The cutting tool will be attached to the tool holder to execute turning.

The front machining tool holder is attached to the sleeve holder 314, and executes a front drilling, tapping and boring action. Power driven tools can be attached to the 4-spindle cross unit 316, providing a rotating motion for drilling, tapping and end milling, etc., to perform cross or front drilling, tapping and milling.

The X-axis performs a diameter direction feed of the tool holder and the tool selection of the 4-spindle cross drilling/milling unit. The Y-axis performs the tool selection of the tool holder, tool selection of the sleeve holder 314 and a diameter direction feed of the 4-spindle cross drilling/milling unit 316.

Figure 3C:
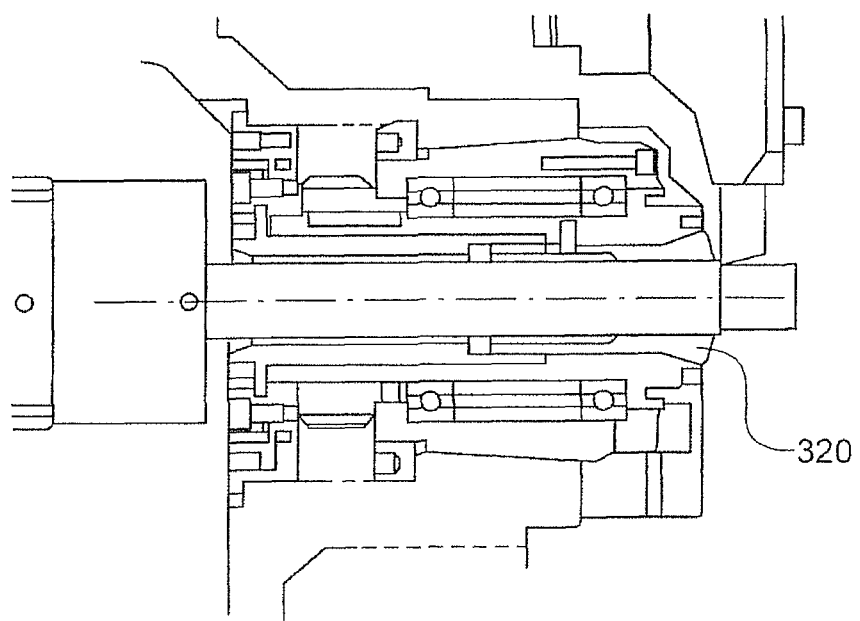
FIG. 3c is a plan view of the revolving guide bush of the screw cutting machine used to manufacture the bone screw of the present principles.

The guide bushing 304 supports a bar near the machining position to prevent material from bending, and thereby helps to achieve highly accurate and reproducible machining. In this unit, the guide bushing 304 supports most of the cutting load in the diametric direction, and the machining accuracy is somewhat dependent on the clearance between the guide bushing 304 and the bar. Therefore, selection of the bar is based on the precision required for the outer diameter of the material being cut with the threads of the present principles. The guide bushing 304 is preferably a revolving guide bush 320 (see FIG. 3c) that is synchronized with the main spindle. Generally the guide bush 320 is positioned within the guide bushing 304.

The sub spindle 313 chucks a bar with the guide bushing (collet) 304 and provides a rotary motion. The sliding unit provides material reciprocation in the ZB-axis direction (longitudinal) and the XB-axis direction with the CNC control.

The tool holder 310 provides ZB-axis direction feed in the back machining, and XB-axis direction feed in the tool selection of sub-spindle unit 308. The various roles of the back attachment machining can be roughly classified as follows:

Non-pip machining: The back attachment chucks a work piece in the cutting process and performs the cutting process by synchronous rotation with the main spindle so as to obtain a cutting-off surface without dowel.

Z-ZB synchronous control: The back attachment chucks a work piece at the same time with the main spindle during the main machining. It also performs a synchronous operation in direction of the Z/ZB-axis, or makes a synchronous rotation with a main spindle so that it suppresses bending or warping of the bar.

Back machining: The live tool holder 306 performs back machining of the cutting-end surface and periphery thereof in cooperation with the back sub-spindle unit 308 of the tool post.

Sub-spindle unit 308 <This is not included in type 540S of the machine>: The tool holder 306 for machining of the cutting-end surface is attached to the back machining sub-spindle unit 308 to perform the backside drilling, tapping and boring. Selecting the drive system for power driven attachment (this is an option) permits the attachment of a power-driven tool until and the machining of the back off-center tapping/milling.

Figure 4:
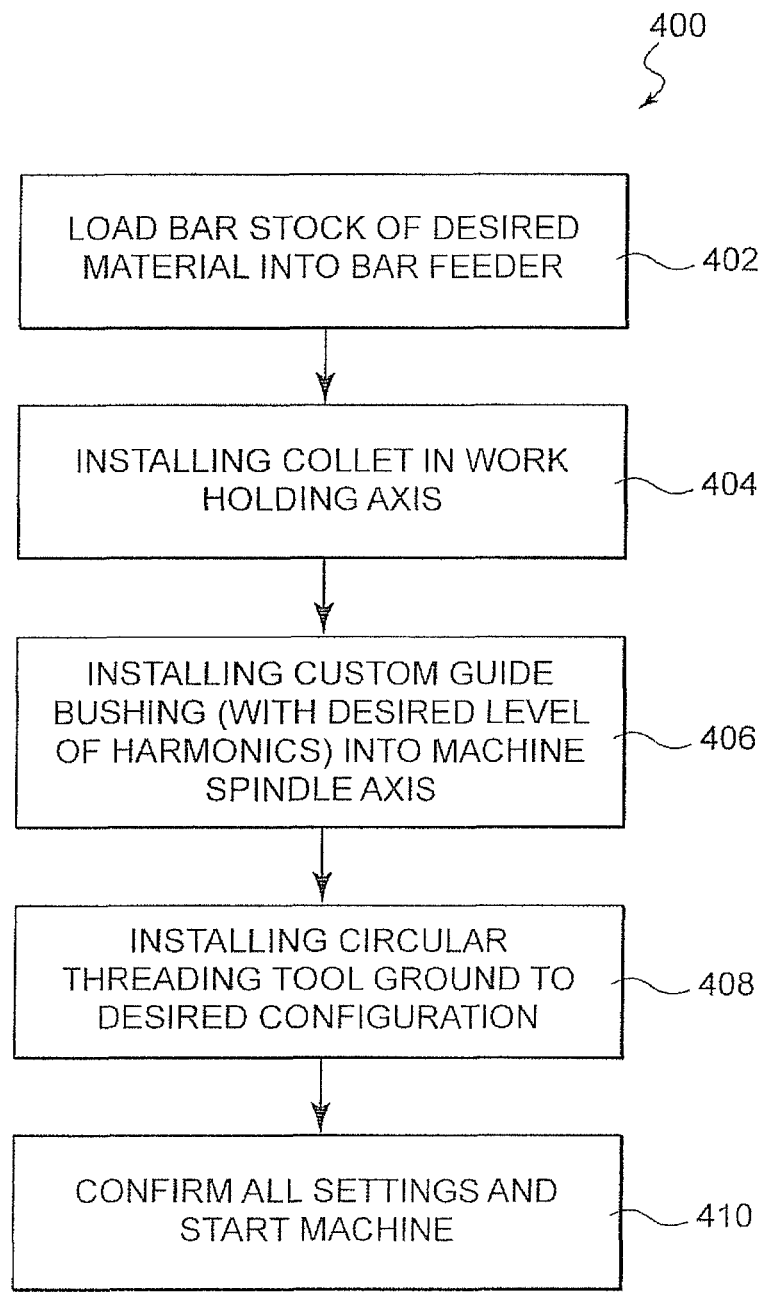
FIG. 4 is a flow diagram of the method for manufacturing a faceted bone screw according to an implementation of the present principles.

FIG. 4 shows the method 400 for manufacturing the faceted bone screw in accordance with a semi-automatic implementation. In accordance with one method of the present principles, a bar stock of desired material is loaded (402) into the bar feeder. A collet is installed (404) in the work holding axis. A custom made guide bushing, fabricated to the size require to produce a desired level of clearance related harmonics, is installed (406) into the machine spindle axis. A circular threading tool which has been ground to produce the desired thread configuration is installed (408) one a live tool holder.

According to one aspect, the facets of the faceted bone screw are applied through a precisely controlled vibratory effect through the application of clearance related harmonics during the screw cutting process. Thus, by adjusting the size of the guide bushing (guide collet) we can define the clearing between the same and the bar stock. This "clearance" generates a clearance related harmonic (or a controlled vibratory effect) as the bar stock is fed through the spindle axis passing by the rotating circular threading tool which is generating the thread configuration onto the bar stock. Through the control of the clearance, the vibratory effect is accurately controlled. Examples of such clearance would be 0.0002-0.005 inches.

Those of skill in the art will recognize that the Swiss type screw machine is a computer programmable machine, and as such, the aforementioned processed can be computer controlled by the machine once programmed accordingly. For example, the machine can be programmed so the threading tool produces the thread configuration in one pass or multiple passes, depending on the size of the bar stock, the amount of material to be machined, and desired finish.

Other multiple features of the faceted bone screw can be performed prior to, or after, the thread configuration is generated onto the bar stock, such as screw head generation, drilling pilot details, drive configurations, coatings and/or any further surface preparation treatments, etc.

Figure 5:
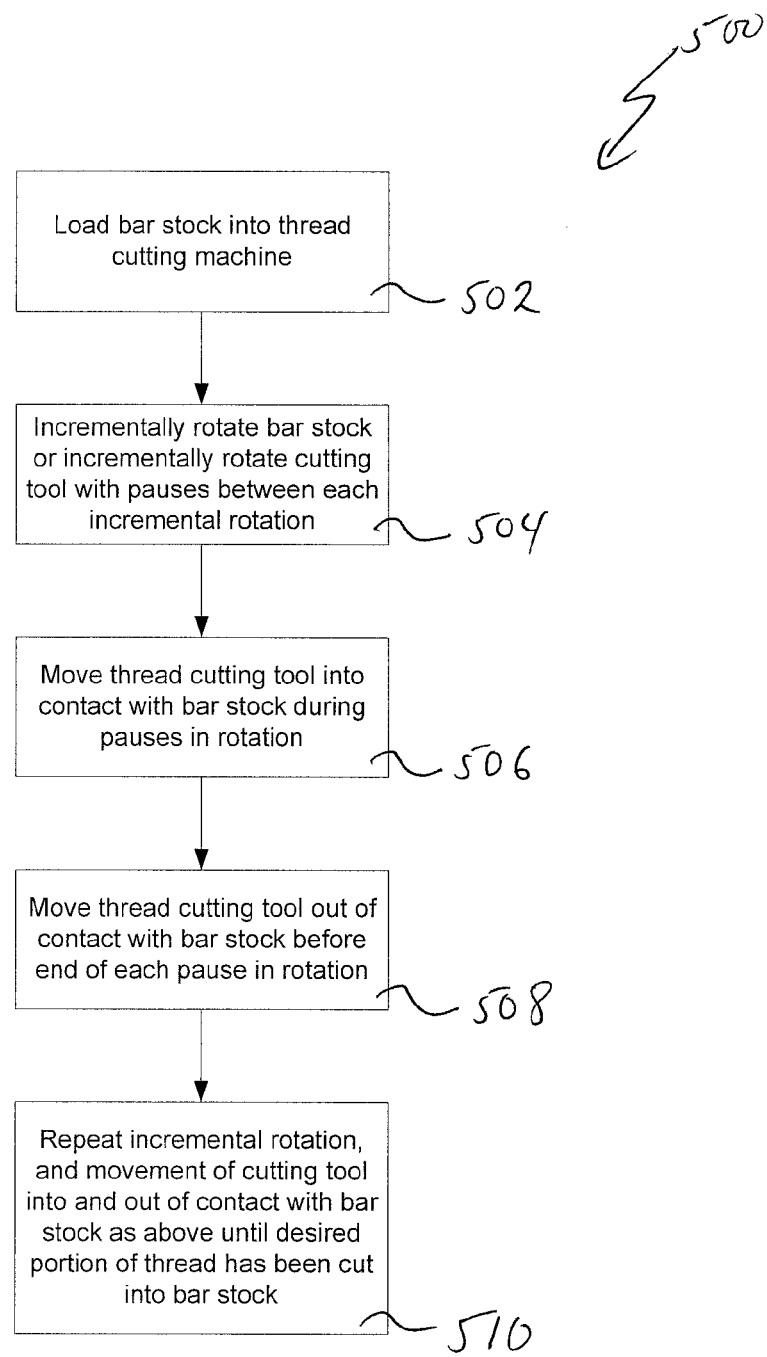
FIG. 5 is a flow diagram of the method for manufacturing a faceted bone screw according to an implementation of the present principles.

FIG. 5 shows another method for manufacturing the bone screw according to the present principles. As mentioned above, in order to manufacture the bone screw in a reproducible, certifiable manner, a precise manufacturing technique is employed using a Swiss type screw machine tool. Although the Swiss type screw machine tool described above is one preferred machine for manufacturing the bone screw of the present principles, other machinery that enables the selective rotation of the bar stock and selective cutting of the same may also be employed without departing from the scope of the invention. According to this method 500, the bar stock is loaded (502) into a thread cutting machine. This loading can be done before or after a head is formed on the bar stock. Once loaded, in one implementation, the bar stock is incrementally rotated with distinct pauses between each incremental rotation (504). In another implementation, the bar stock is stationary and the cutting tool is incrementally rotated around the bar stock. The time duration for each pause between incremental rotations of either the bar stock or the cutting tool can be varied depending on the desired thread design and configuration. Such time duration can be anywhere from 0.1-5 seconds. During each pause, the thread cutting tool is moved into contact with the bar stock to cut the thread for the same (506). The movement of the cutting tool into contact with the bar stock can be performed radially with respect to the bar stock, or could be angularly offset from a radial approach so as to enable variations in the thread designs to be described below with respect to FIGS. 6-20. In this manner, the depth (or radial penetration) of the cutting tool into the bar stock can be infinitely varied (without compromising the integrity of the bar stock used to create the screw), thus creating different radii (i.e., measured from the center of the screw shaft—see for example FIG. 2b) throughout the cutting of the thread resulting in the faceted screw configuration. Once the cutting is completed for that pause period, the cutting tool is moved away from the bar stock (508), and the cycle is repeated (510) until the desired portion of the thread has been cut into the bar stock.

In accordance with the above noted implementation where the bar stock is held stationary, a rotating cutting head/tool is controlled to impart the thread cutting that is performed with predetermined time periods between cutting actions. Here, the rotating cutting tool may be rotated anywhere from 0.01-90 degrees before imparting the cutting to the stationary bar stock. The radial penetration of the rotating cutting tool into the bar stock can also be varied in order to impart the faceted configuration to the bar stock. Each cutting action will be performed for a predetermined amount of time before moving the cutting head out of contact with the bar stock. For example, after a first cutting action, the rotating cutting tool is moved out of contact with the stationary bar stock, rotated a predetermined amount, and then brought back into contact with the stationary bar stock for another predetermined amount of time to implement the second cutting action on the next portion of the thread. Those of skill in the art will appreciate that two adjacent cuts of however slight differing radii will result in the formation of adjacent concave thread cuts, thereby forming the concave facets in the same.

Figure 6:
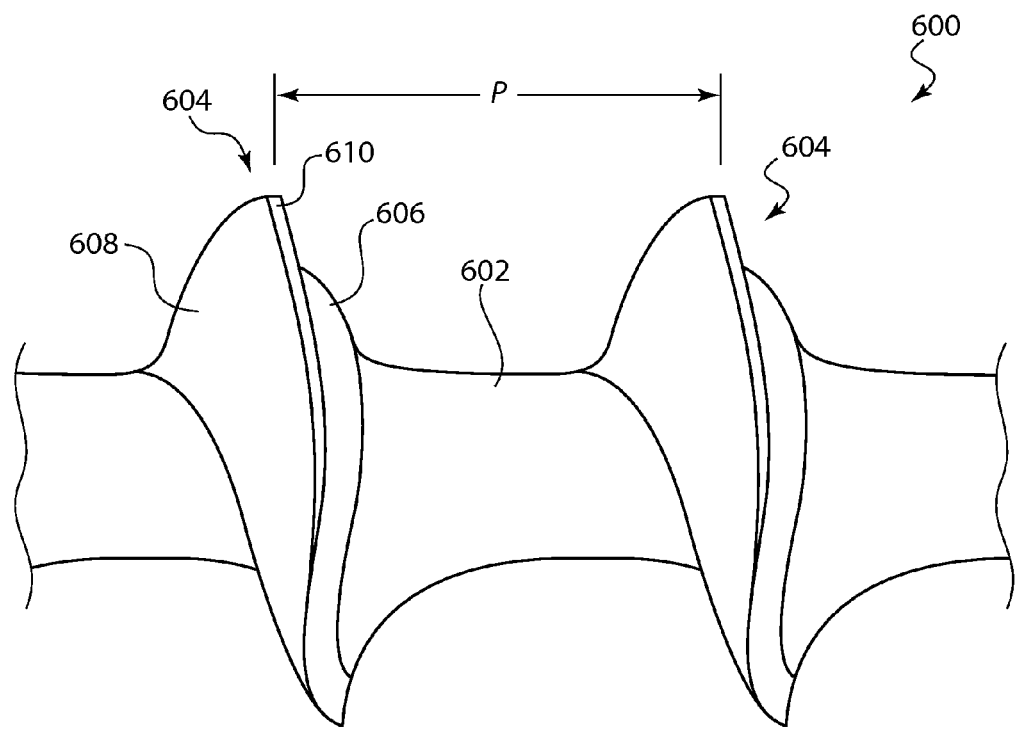
FIG. 6 is side view of a two threads of a screw for purposes of describing the various portions thereof used herein.

FIG. 6 shows a side view of a portion of a threaded fastener 600 for showing the various parts of the same. Those of skill in the art will clearly recognize that any threaded fastener has a thread pitch P which is the distance between adjacent threads 604. A shaft 602 is essentially the remaining portion of the bar stock between the threads 604 formed therein. Each thread 604 includes a leading face/surface 606 and a trailing face/surface 608, usually connected at the peak or crest 610. As will be described below with reference to the remaining embodiments, any one or more combinations of the following embodiments may be made to a single bone/orthopedic screw without departing from the scope of present principles as disclosed herein.

Figure 7:
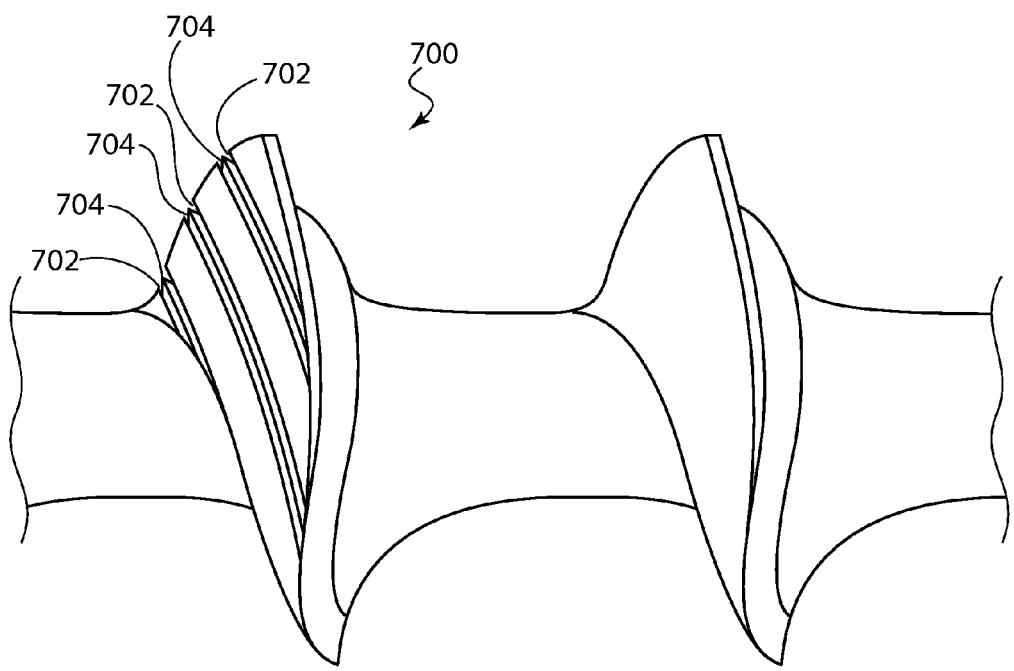
FIG. 7; is a side view of a thread configuration for a bone/orthopedic screw according to an implementation of the present principles.

FIG. 7 shows an implementation of a bone/orthopedic screw 700 where one or more grooves 702 are cut into the trailing face of the thread. Within each groove 702 is an additional thread 704 of any preferred configuration. In the example shown, the additional thread 704 has an upside down V cross section. By cutting the grooves 702 into the trailing face of the thread, the surface area of the same is increased. By adding the internal thread 704, there is now additional surface area to which the bone may adhere, and increase further osteointegration with the same. According to an exemplary implementation, the grooves 702 are spaced from each other but sufficiently close enough to each other to create a pitch between the side faces of two adjacent grooves. In other words, the material between adjacent grooves 702 forms a crest, which adds a smaller recessed thread within the trailing face of the larger threads.

Figure 8:
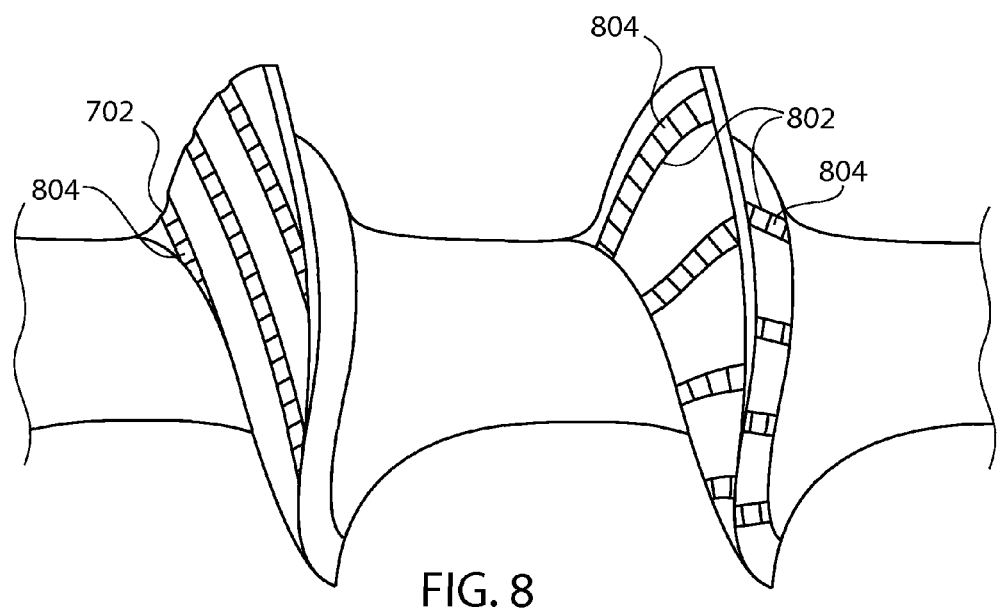
FIG. 8 is a side view of two thread configurations for a bone/orthopedic screw according to another implementation of the present principles.
Figure 9A:
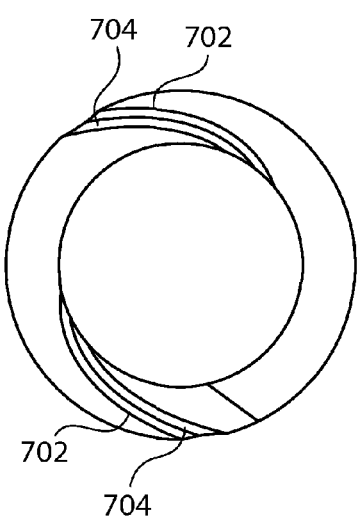
FIGS. 9a and 9b are cross sectional views of the two thread configurations shown in FIG. 8.
Figure 9B:
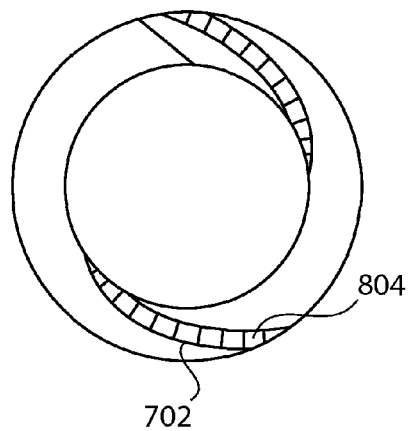

FIG. 8 shows alternative implementations for the added groove 702. On the left example, the groove 702 is circumferentially cut into the trailing face of the thread, and can include one or more facets 804 cut into the same. On the right example, the grooves 802 are cut radially into the trailing face and leading face of the screw threads and may also include one or more facets 804 cut into the same. FIGS. 9a and 9b show cross sectional views of the left and right examples of FIG. 8 showing the circumferential groove 704. In this implementation, the addition of the grooves 702 or 802 increases the surface area of the larger thread and maximizes the area available for introduction of facets in an otherwise non-faceted screw.

Figure 10:
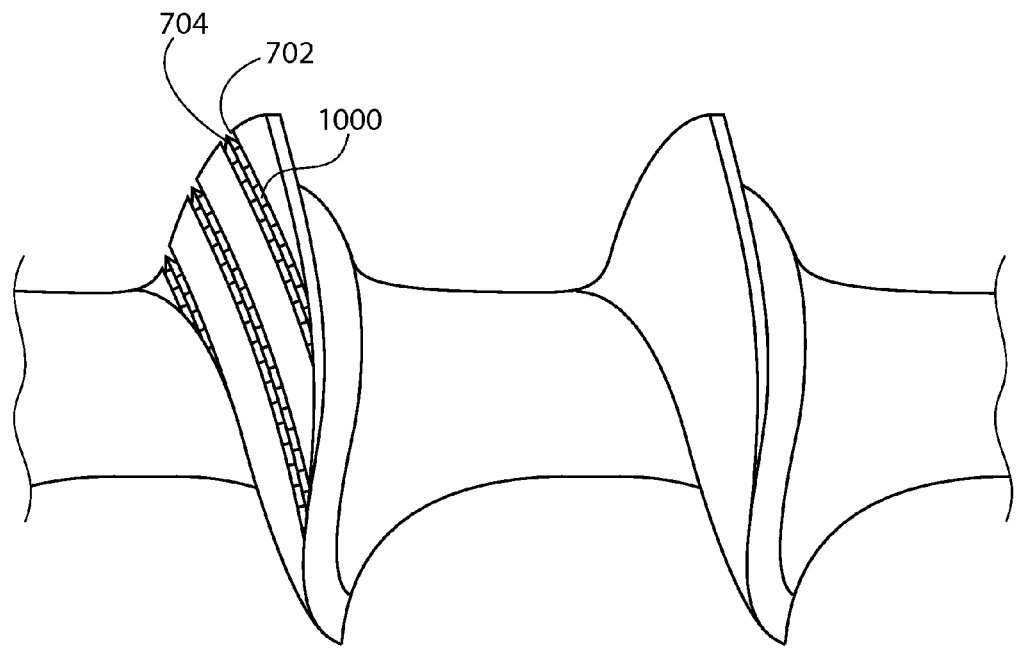
FIG. 10 is a side view of a thread configuration for a bone/orthopedic screw according to another implementation of the present principles.

FIG. 10 shows a modified implementation of the embodiment shown in FIG. 7 where the additional thread 704 includes one or more facets 1000 on the surfaces thereof. Again, the addition of groove 702 with the thread 704 contained therein increases the available surface area of the trailing face of the thread. The further addition of facets 1000 further increases the already increased surface area of the thread 704.

Figure 11:
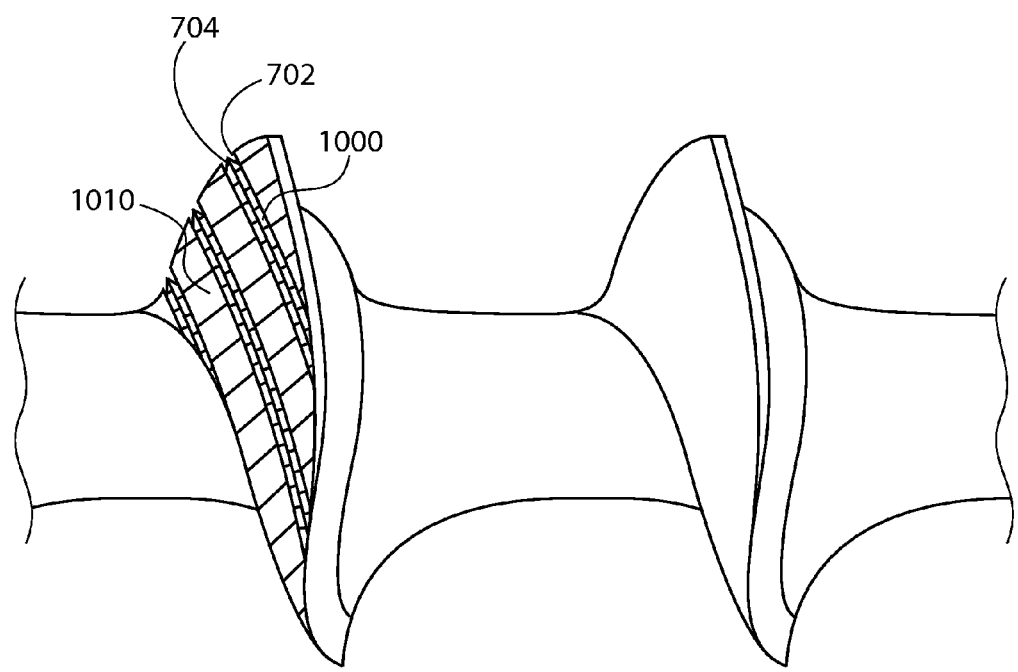
FIG. 11 is a side view of a thread configuration for a bone/orthopedic screw according to another implementation of the present principles.

FIG. 11 shows a further modified implementation of the embodiment shown in FIG. 10. In this implementation, the remaining space between the grooves 702 on the trailing face of the thread includes more or more facets 1010.

Figure 12A:
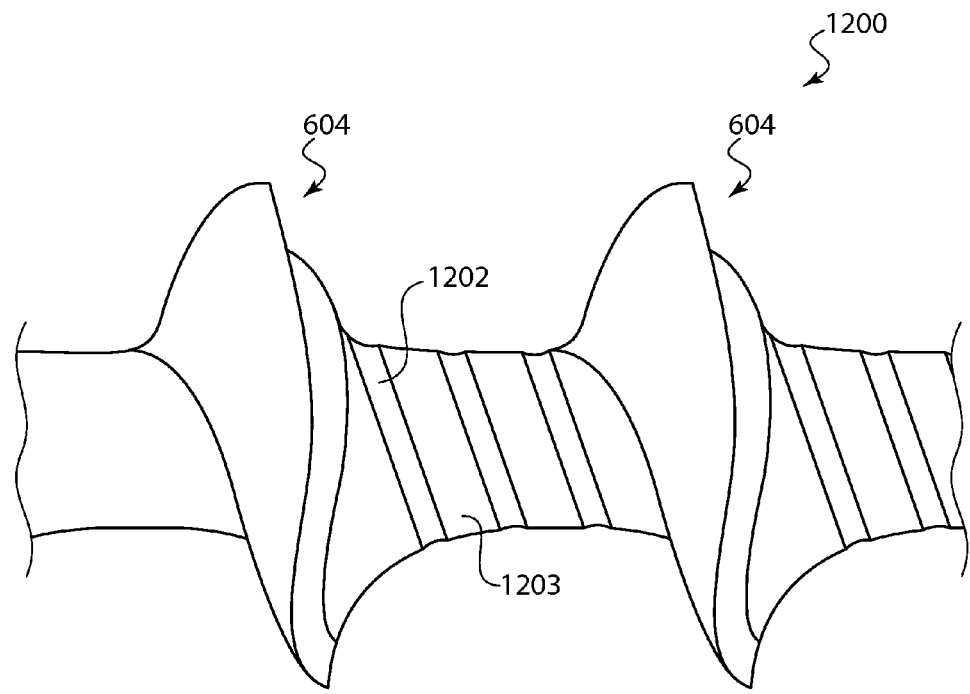
FIG. 12a is a side view of a thread configuration for a bone/orthopedic screw according to another implementation of the present principles.

FIG. 12a shows an implementation of the bone/orthopedic screw 1200 according to the present principles. Here, a spiral groove 1202 is added to the shaft between adjacent threads.

Figure 12B:
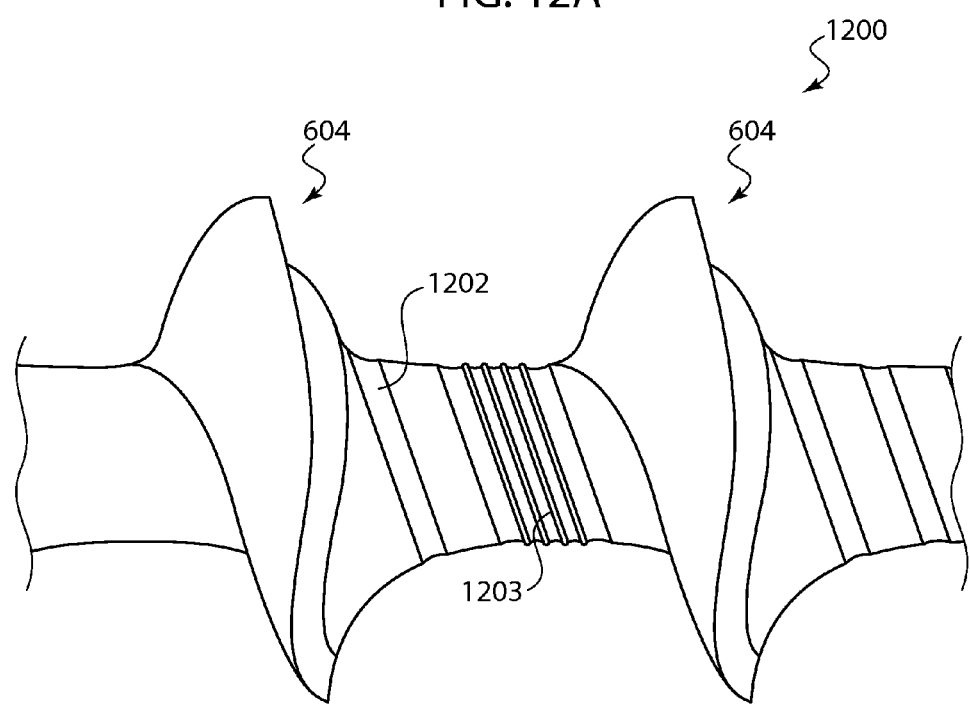
FIG. 12b is a side view of a thread configuration for a bone/orthopedic screw according to another implementation of the present principles.
Figure 12C:
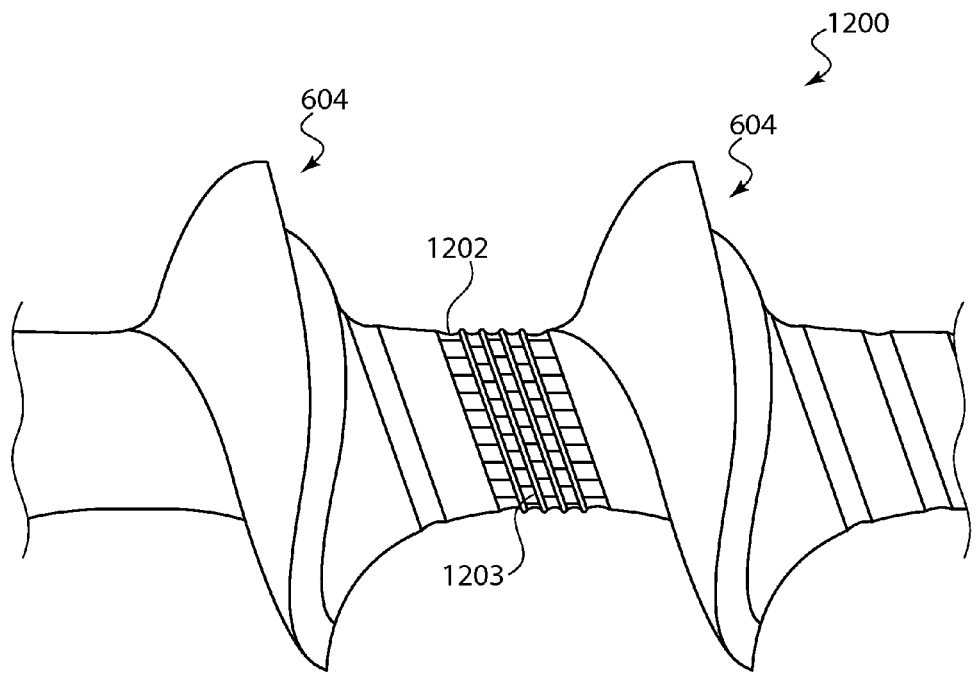
FIG. 12c is a side view of a thread configuration for a bone/orthopedic screw according to another implementation of the present principles.

The spiral groove 1202 increases the surface area of the shaft portion between the threads. In this example, the size of space 1203 between the grooves 1202 can be changed according to any preferred design configuration. For example, it is herein contemplated that the spacing 1203 can be in a range of 0.001-0.5 inches depending on the spacing of the respective threads 604. FIGS. 12b and 12c show this concept where the spacing 1203 has been reduced such that groove 1202 essentially forms another thread within the shaft of the screw. Here, each space 1203 functions as the crest or peak of the new thread created by the groove 1202. In the example of FIG. 12c, facets are added to the groove 1202, and could also be added to the surface of the crest formed by the space 1203 between the grooves 1202. Here, the added groove does not extend beyond the shape of the original screw/shaft, and is an addition to the same (i.e. is recessed into the existing shaft of the threaded screw).

Figure 13:
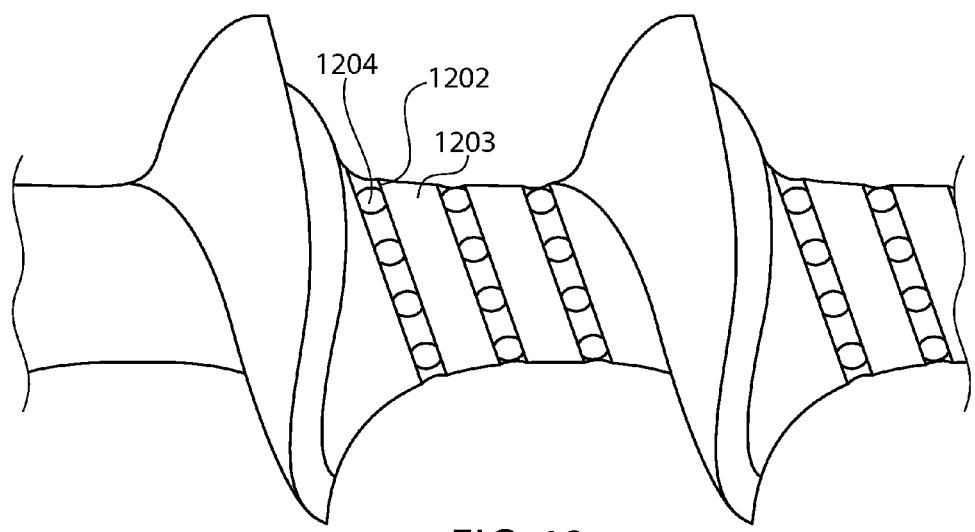
FIG. 13 is a side view of a thread configuration for a bone/orthopedic screw according to another implementation of the present principles.
Figure 14:
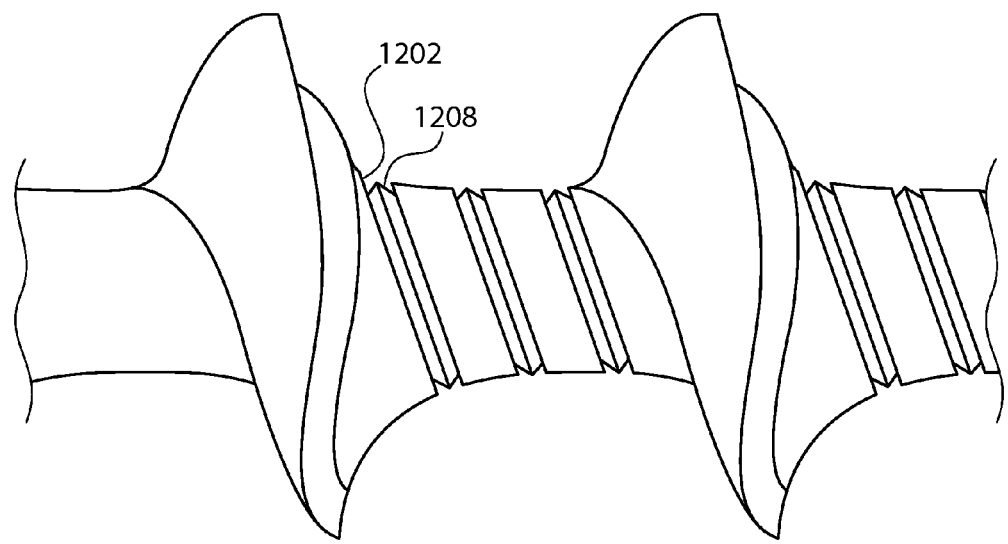
FIG. 14 is a side view of a thread configuration for a bone/orthopedic screw according to another implementation of the present principles.
Figure 15:
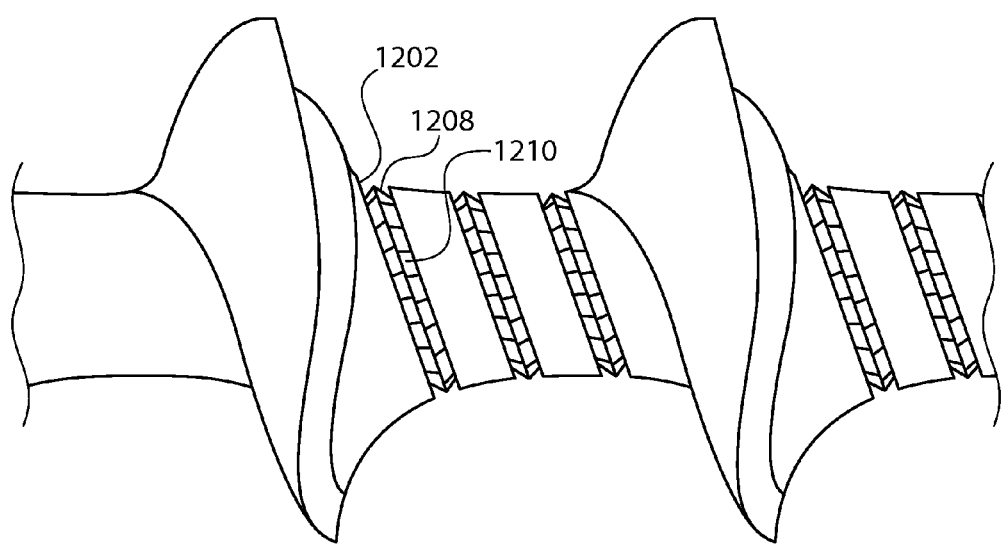
FIG. 15 is a side view of a thread configuration for a bone/orthopedic screw according to another implementation of the present principles.
Figure 16:
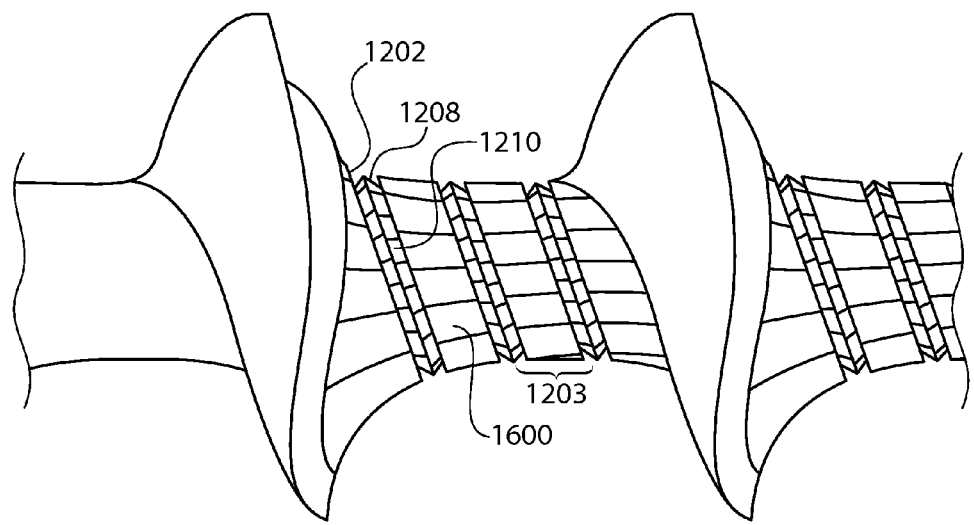
FIG. 16 is a side view of a thread configuration for a bone/orthopedic screw according to another implementation of the present principles.

FIG. 13 shows another implementation where one or more facets 1204 are added to the groove 1202. FIG. 14 shows the groove 1202 with the added thread 1208 disposed therein. The additional thread 1208 (or upside down V cross section) operates to further increase the exposed surface area of the groove 1202. FIG. 15 shows the thread 1208 having one or more facets 1210 on one or both of the respective faces thereof. FIG. 16 shows a further modification where the spacing 1203 includes one or more facets 1600. In another exemplary implementation (as shown in FIGS. 12b and 12c), the space 1203 is very small between adjacent spiral grooves 1202, such that the space 1203 itself forms a crest between the adjacent spiral groove 1202. This crest will further function as a slightly larger diameter thread between the grooves formed in the shaft.

Figure 17:
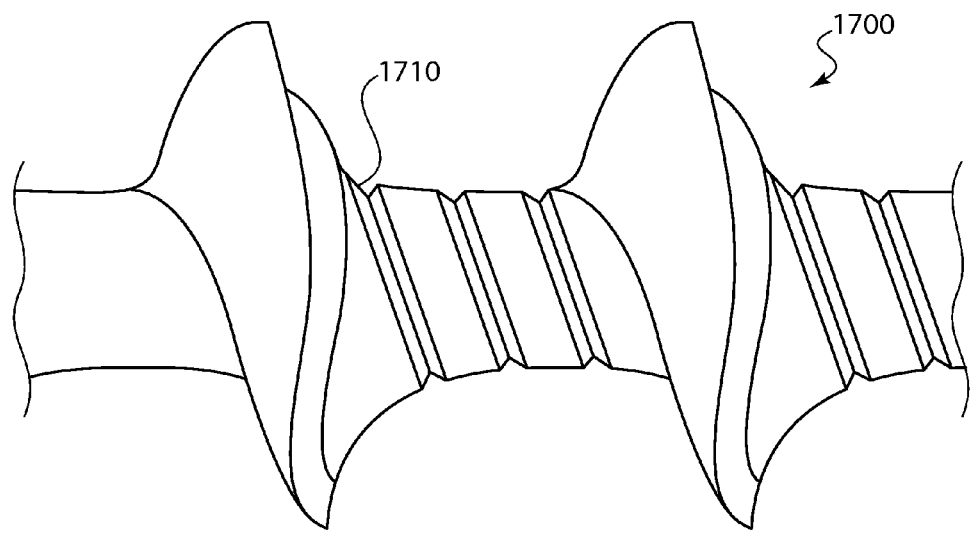
FIG. 17 is a side view of a thread configuration for a bone/orthopedic screw according to another implementation of the present principles.
Figure 18:
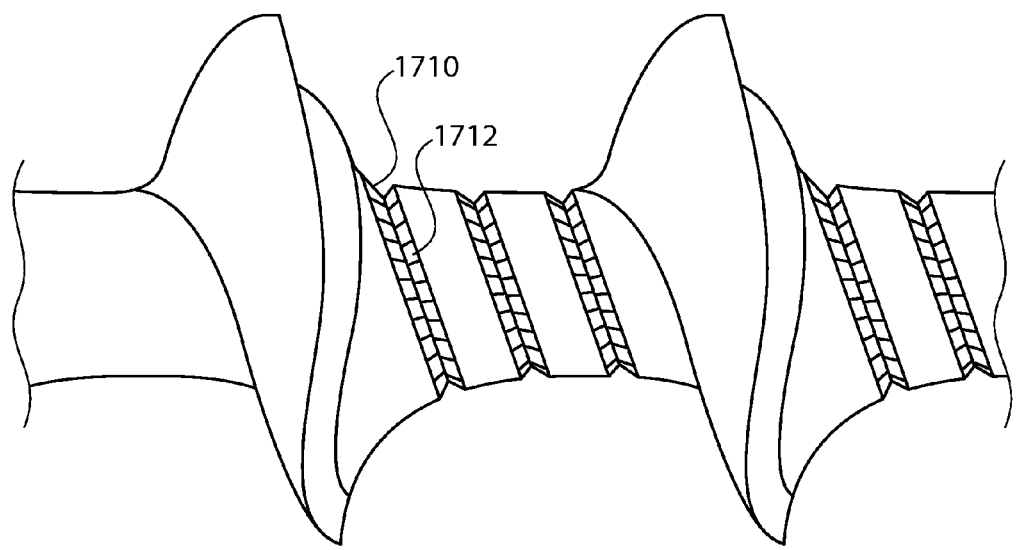
FIG. 18 is a side view of a thread configuration for a bone/orthopedic screw according to another implementation of the present principles.

FIGS. 17 and 18 show another implementation of the bone/orthopedic screw 1700 according to the present principles. Here the groove 1710 is V shaped in cross section. One or more facets 1712 can be added to either or both surfaces of the V-shaped groove (FIG. 18). As with the embodiment shown in FIGS. 12b and 12c, the spacing between adjacent grooves 1710 can be such that the crest between adjacent grooves could function as a crest or peak of an internal thread formed by the groove 1710.

Figure 19:
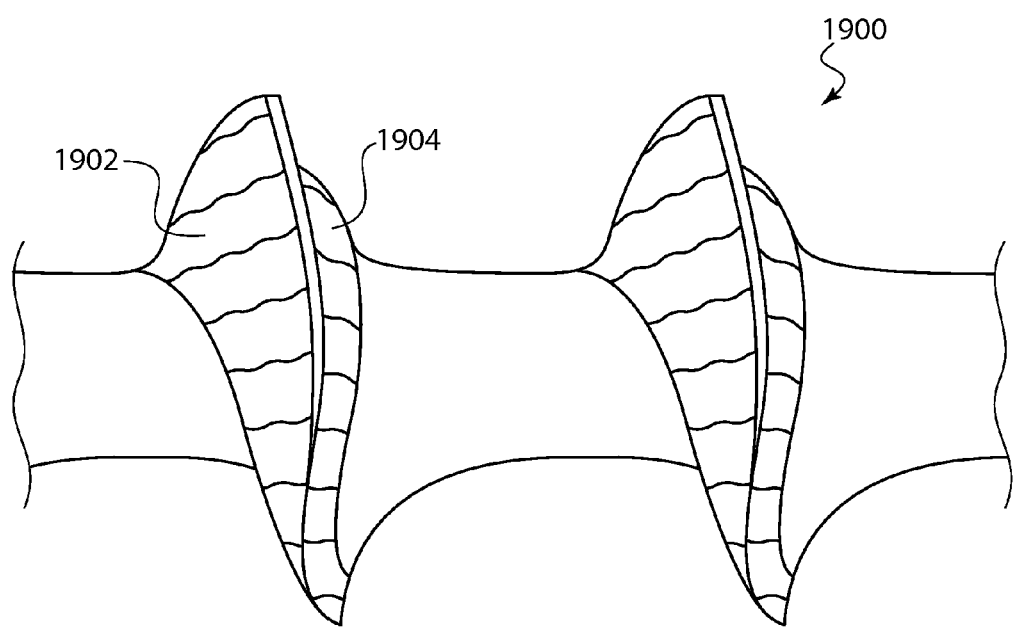
FIG. 19 is a side view of a thread configuration for a bone/orthopedic screw according to another implementation of the present principles.
Figure 20:
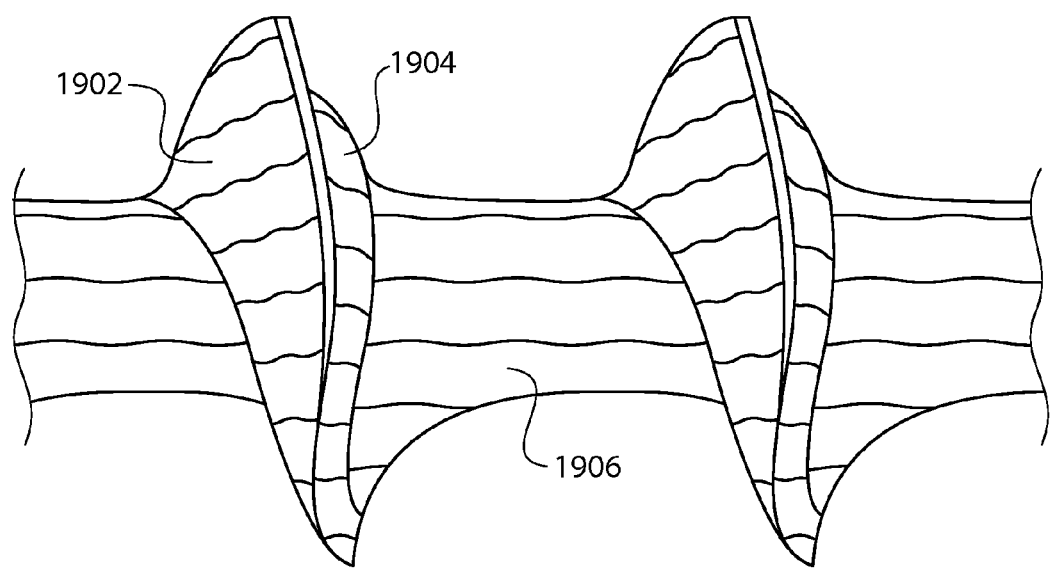
FIG. 20 is a side view of a thread configuration for a bone/orthopedic screw according to another implementation of the present principles.

FIGS. 19 and 20 show yet another implementation of the bone/orthopedic screw 1900, according to the present principles. Here, facets 1902 can be added to the trailing face of the thread, and/or facets 1904 can be added to the leading face of the thread. In the implementations shown, these facets are radially disposed on the trailing face or leading face of the thread, however as described above with respect to the several other contemplated implementations; the facet configurations can be circumferential, longitudinal and/or radial without departing from the intended scope of the invention. In addition to the facets 1902 and 1904, the shaft of the screw between the threads can also include facets 1906.

Figure 21A:
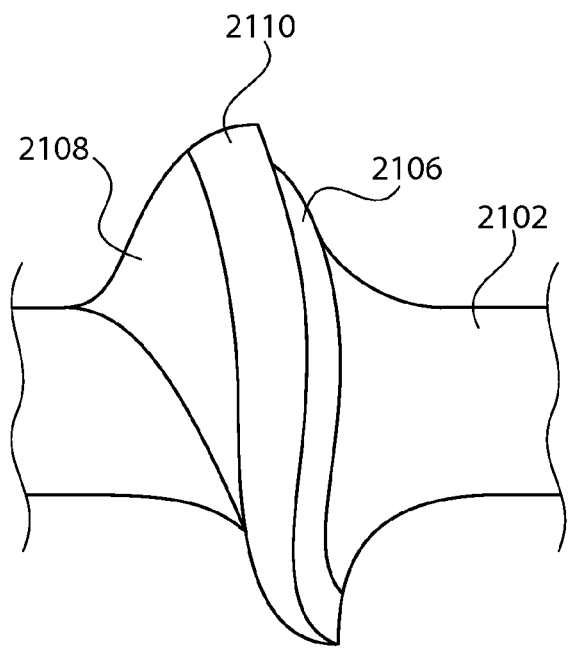
FIGS. 21a and 21b show a side view of a thread configuration for a bone/orthopedic screw according to another implementation of the present principles.
Figure 21B:
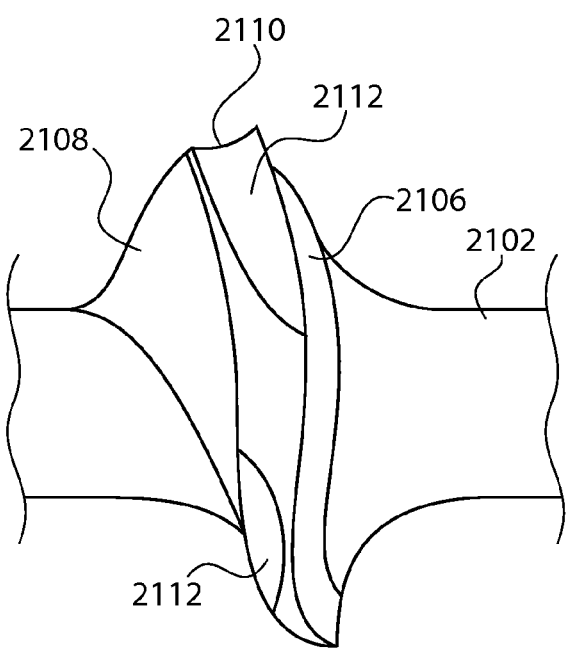

FIG. 21a shows an alternative configuration of the bone screw thread where the peak or crest 2110 of the thread is enlarged between the trailing face 2108 and the leading face 2106. FIG. 21b shows a further implementation where a groove 2112 is cut into the enlarged peak/crest 2110. This will operate to increase the surface area of the peak/crest 2110 and significantly increase the osteointegration capability of the same.

Those of skill in the art will appreciate that the above variations of the bone screw and the use of additional grooves and/or different facet configurations may be mixed and matched according to a desired or specific application to which the bone screw will be used. Such applications can include, but are clearly not limited to cortical screws, cancellous screws, headless compression screws, external fixation screws and/or pins, guide wires, implants, implant anchors, etc.

In accordance with other contemplated implementations, the bone/orthopedic screw and/or the grooves cut therein of the present principles may be further coated, treated and/or applied with various types of coatings/treatments which provide further enhancement to the respective applications of the bone screw. Here, these coatings could be applied to any part or portion of the bone screw.

For example, the bone screw of the present principles may be manufactured and then coated with medications or other treatments that promote osteointegration, prevent infection and/or deliver one or more medications in one or more varying volumes to the areas around the bone screw (i.e., either the areas of bone around the screw that is inserted into the bone and/or the areas of bone screw that are not within the bone but are still within the patient's body). Some examples of such coatings and method for applying them can be found in U.S. Pat. Nos. 7,875,285, 7,879,086, 8,028,646, 7,913,642 and 7,901,453, each of which is incorporated herein by reference. Those of skill in the art will appreciate that any coating or treatment could be added to the bone/orthopedic screw of the present principles without departing from the scope of the same. This may include films or coatings that dissolve once within the human body. Other possible coatings or files may also include those that facilitate bone growth (e.g., bone growth hormones).

Those of skill in the art will recognize that the "bar stock" referred to throughout this specification is the material which the orthopedic/bone screw is made of Examples of this material, as they are currently being used are Titanium, Stainless Steel, cobalt chromium, and absorbable biocompatible plastics. The present principles may also be applied to any known or not yet known material used for orthopedic/bone applications. It is further contemplated herein that the head of the bone screws and or the tips can be made in any preferred form for a particular bone application/penetration without departing from the intended scope of the present principles. It is also contemplated that the bar stock on which the threads of the present principles are applied may also be hollow and may include internal threads for connection of other fixation devices, or orthopedic alignment devices, etc.

It is to be understood that the present principles may be implemented in various forms of hardware, software, firmware, special purpose processors, or a combination thereof. Preferably, the present principles may be implemented as a combination of hardware and software. Moreover, the software is preferably implemented as an application program tangibly embodied on a program storage device. The application program may be uploaded to, and executed by, a machine comprising any suitable architecture. Preferably, the machine is implemented on a computer platform having hardware such as one or more central processing units (CPU), a random access memory (RAM), and input/output interface(s). The computer platform also includes an operating system and microinstruction code. The various processes and functions described herein may either be part of the microinstruction code or part of the application program (or a combination thereof) that is executed via the operating system. In addition, various other peripheral devices may be connected to the computer platform such as an additional data storage device and a printing device.

It is to be further understood that, because some of the constituent system components and method steps depicted in the accompanying Figures are preferably implemented in software, the actual connections between the system components (or the process steps) may differ depending upon the manner in which the present principles is programmed. Given the teachings herein, one of ordinary skill in the related art will be able to contemplate these and similar implementations or configurations of the present principles.

While there have been shown, described and pointed out fundamental novel features of the present principles, it will be understood that various omissions, substitutions and changes in the form and details of the methods described and devices illustrated, and in their operation, may be made by those skilled in the art without departing from the spirit of the same. For example, it is expressly intended that all combinations of those elements and/or method steps which perform substantially the same function in substantially the same way to achieve the same results are within the scope of the present principles. Moreover, it should be recognized that structures and/or elements and/or method steps shown and/or described in connection with any disclosed form or implementation of the present principles may be incorporated in any other disclosed, described or suggested form or implementation as a general matter of design choice. It is the intention, therefore, to be limited only as indicated by the scope of the claims appended hereto.

What is claimed is:

1. An orthopedic screw comprising:
   a shaft;
   a thread cut into at least a portion of said shaft, said threads having a leading edge, a trailing edge and a depth; and
   at least one groove formed in one of the leading edge or the trailing edge and configured to increase a surface area of the respective leading or trailing edge; wherein the at least one groove is cut into the leading or trailing edge of the thread so as to extend radially outward from the shaft.

2. The orthopedic screw of claim 1, wherein the at least one groove is cut into the leading or trailing edge of the thread, the at least one groove having a varying depth throughout the groove.

3. The orthopedic screw of claim 1, wherein said at least one groove has a V-shaped cross section.

4. The orthopedic screw of claim 1, wherein the at least one groove has an upside down V-shaped cross section.

* * * * *